United States Patent [19]

Shah

[11] Patent Number: 5,247,827
[45] Date of Patent: Sep. 28, 1993

[54] RESISTIVE MEASUREMENT OF AIRBORNE CONTAMINANTS

[75] Inventor: Bharatbhai M. Shah, Matawan, N.J.

[73] Assignee: Bell Communications Research, Inc., Livingston, N.J.

[21] Appl. No.: 868,552

[22] Filed: Apr. 14, 1992

[51] Int. Cl.$^5$ .............................. G01N 15/00
[52] U.S. Cl. .................................. 73/28.01
[58] Field of Search ............... 73/28.01, 28.02, 28.04, 73/61.42, 53.07; 340/607

[56] References Cited

U.S. PATENT DOCUMENTS

| | | |
|---|---|---|
| 3,262,106 | 7/1966 | Crawford et al. ............... 73/28.01 |
| 3,424,977 | 1/1969 | Krobath . |
| 3,472,080 | 10/1969 | Webb ............................ 73/28.01 X |
| 3,520,172 | 7/1970 | Liu et al. . |
| 3,718,029 | 2/1973 | Gourdine et al. . |
| 3,794,909 | 2/1974 | Smith . |
| 4,087,743 | 5/1978 | Bressan . |
| 4,098,112 | 7/1978 | Kramer . |
| 4,117,715 | 10/1978 | Hoenig . |
| 4,158,610 | 6/1979 | Bauer et al. . |
| 4,400,971 | 8/1983 | Tassicker . |
| 4,822,465 | 4/1989 | Jones et al. . |

FOREIGN PATENT DOCUMENTS

| | | | |
|---|---|---|---|
| 0159094 | 10/1985 | European Pat. Off. ........... | 73/61.42 |
| 839111 | 5/1952 | Fed. Rep. of Germany ..... | 73/28.01 |
| 39543 | 3/1985 | Japan .................. | 73/28.01 |
| 953355 | 8/1982 | U.S.S.R. ............... | 73/61.42 |

OTHER PUBLICATIONS

"Test Methods Manual," The Institute for Interconnecting and Packaging Electronic Circuits, Nos. 2.4.37.1, 2.5.27, 2.6.3, 2.6.3.1, 2.6.3.2, and 2.6.3.3 at pp. B-8, B-9; D-5, D-6; and VE-8 to F-7.

Primary Examiner—Hezron E. Williams
Assistant Examiner—Joseph W. Roskos
Attorney, Agent, or Firm—Leonard Charles Suchyta; James W. Falk

[57] ABSTRACT

An apparatus and method for measuring conductive airborne particulates in which a filter (16) having a pair of interdigitated electrodes (18, 20) printed on its surface is placed in a sampling chamber (14). A pump (10) draws air (12) through the chamber and through the filter with airborne particles being deposited on the side of the filter with the electrodes. The resistance between the electrodes is measured (22) without removing the filter from the chamber.

10 Claims, 2 Drawing Sheets

RESISTIVE MEASUREMENT OF AIRBORNE CONTAMINANTS

FIELD OF THE INVENTION

The invention relates generally to the measurement of airborne particles. In particular, the invention relates to the electrical characterization of airborne particles.

BACKGROUND ART

Computer-based automation has promoted the installation of large quantities of sophisticated electronics in environments of less than optimal quality. For example, modern telephone central offices and switching offices are relatively large buildings filled with racks of electronic circuits mostly assembled on printed circuit boards. An increasing fraction of the local telephone switching equipment is being located in remote sites, such as buried vaults. In both cases, the need for reliable operation of the electronics has dictated that the environment be relatively benign. Hence, not only are the temperature and humidity controlled, but the air circulation is controlled so as to minimize the incursion of dust from the outside while also exhausting internally generated particles and vapors.

Nonetheless, dust remains a problem for electronic circuitry, especially when its useful lifetime is measured in decades. In this discussion, dust will be considered to be any solid airborne particle regardless of source. A principal failure mechanism in printed circuits is an unacceptable increase in leakage current caused by dust bridging neighboring electrical leads which should be electrically isolated. Either the dust itself electrically conducts, or it absorbs water vapor after its deposition, resulting in electrical conduction. In either case, the accumulated dust increases leakage current. The dust may accumulate over long periods of routine operation or may be deposited by a specific disaster, which may range from a fire to a failure of the air filtration system. Usually the dust can be cleaned from the printed circuit boards, but any cleaning is labor intensive and thus partially defeats the automation effort.

Gourdine et al. have disclosed in U.S. Pat. No. 3,718,029 an automated apparatus to measure the amount of dust, but this apparatus does not directly measure the dust's conductivity. Hoenig has disclosed in U.S. Pat. No. 4,117,715 an apparatus for determining the polarity of charge carried by dust but does not determine the conductivity. The Institute for Interconnecting and Packaging Electronic Circuits has promulgated standard IPC-TM-650, which defines multi-purpose test board IPC-B-25. The board consists of an interdigitated electrode pattern printed on the surface of an insulating board. This test board is commonly used in the electronic manufacturing industry to ensure that the contaminant level remain at or below a prescribed level.

SUMMARY OF THE INVENTION

The invention may be summarized as a method and apparatus for detecting the conductivity of particulate matter, such as dust, carried in air or other gases. Air is pumped through a filter having a mesh size sufficiently small to filter out the particles. An interdigitated electrode structure is formed on the upstream side of the filter. The conductivity of the dust is determined by measuring the electrical resistance between the electrodes.

DETAILED DESCRIPTION OF THE PREFERRED EMBODIMENTS

Figure 1:
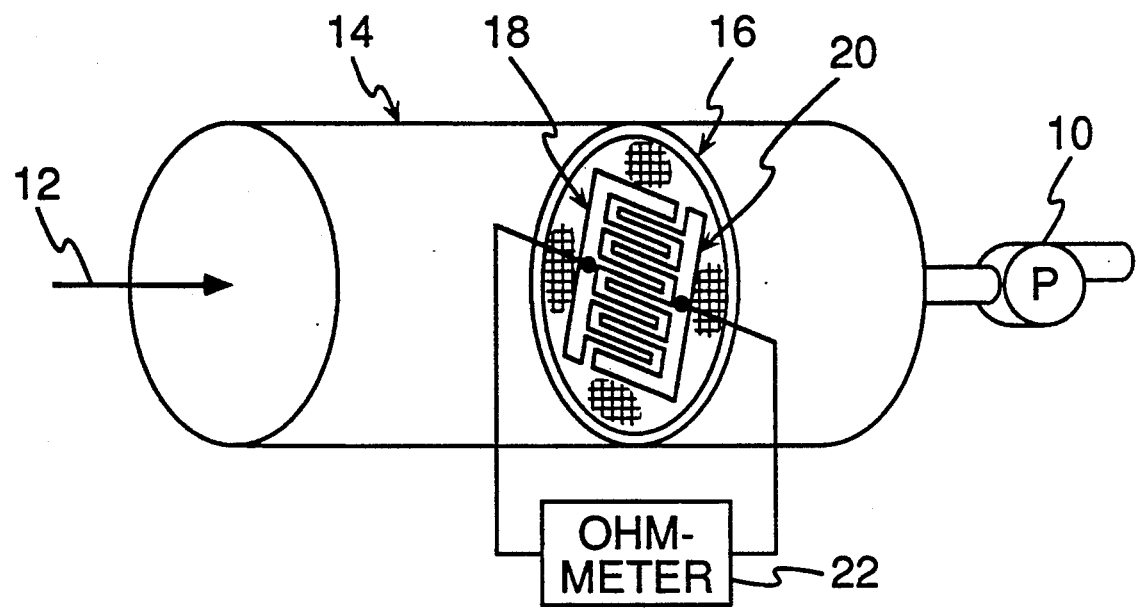
FIG. 1 is a schematic illustration of the conductive dust detection system of the invention.

The general principle of the invention is illustrated in the schematic illustration of FIG. 1. An air pump 10 of predetermined pumping capacity pulls ambient air as an air flow 12 through a closed conduit 14. A mesh filter element 16 intercepts the air flow 12 and has a mesh size sufficiently small so as to trap particles carried in the air flow 12 on its upstream surface. Two interdigitated electrodes 18 and 20 are preformed on the upstream surface of the filter element 16 and, at least during readout, are connected to respective terminals of an ohmmeter 22 or other resistance-measuring device.

The resistance measured by the ohmmeter 22 is a direct measure of the conductivity of the dust filtered out by the filter element 16. The less the resistance is, the greater is the problem with leakage currents resulting from conductive dust. A particular environment can be monitored by operating the pump 10 for a set time with a clean filter element 16 and associating the measured resistance with that environment.

Figure 2:
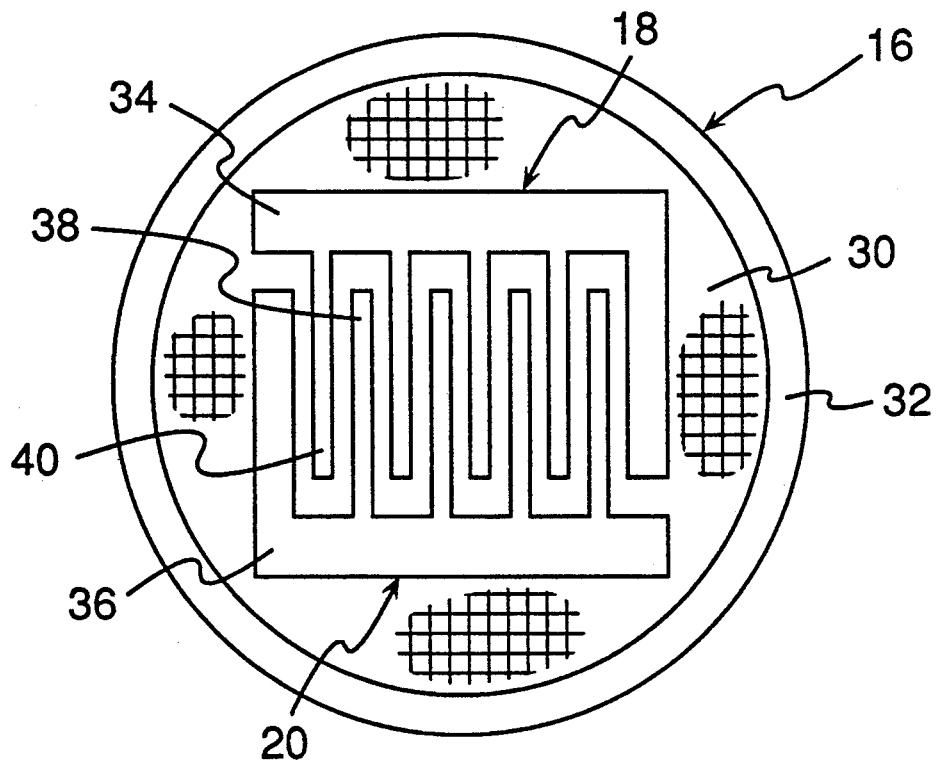
FIG. 2 is a plan view of a filter element of the invention having an electrode pattern printed on its surface.

An example of the filter element 16 is illustrated in the plan view of FIG. 2. A porous membrane 30 is fused to a plastic collar 32. The filter described to this point is commercially available as part number R2PJ037 from Gelman Sciences, Inc. of Ann Arbor, Mich. under the trade name Teflo filter. The porous membrane 30 of this filter is composed of teflon with a pore size (diameter) of 2 $\mu$m. It has an overall diameter of 3.7 cm. Silk screening using a conductive silver-based flexible ink, type A3706 from Engelhard Industries, Inc. of Newark, N.J., then prints an electrode pattern on a side of the mesh 30. The printed electrode pattern is sufficiently thick so as to have relatively negligible resistance compared to the dust being measured. The electrode pattern consists of a pair of interdigitated electrodes 18 and 20 each consisting of a pad 34 or 36 and five electrode fingers 38 or 40. A complementary pair of electrode fingers 38 and 40 are separated by a distance of 0.5 mm.

Figure 3:
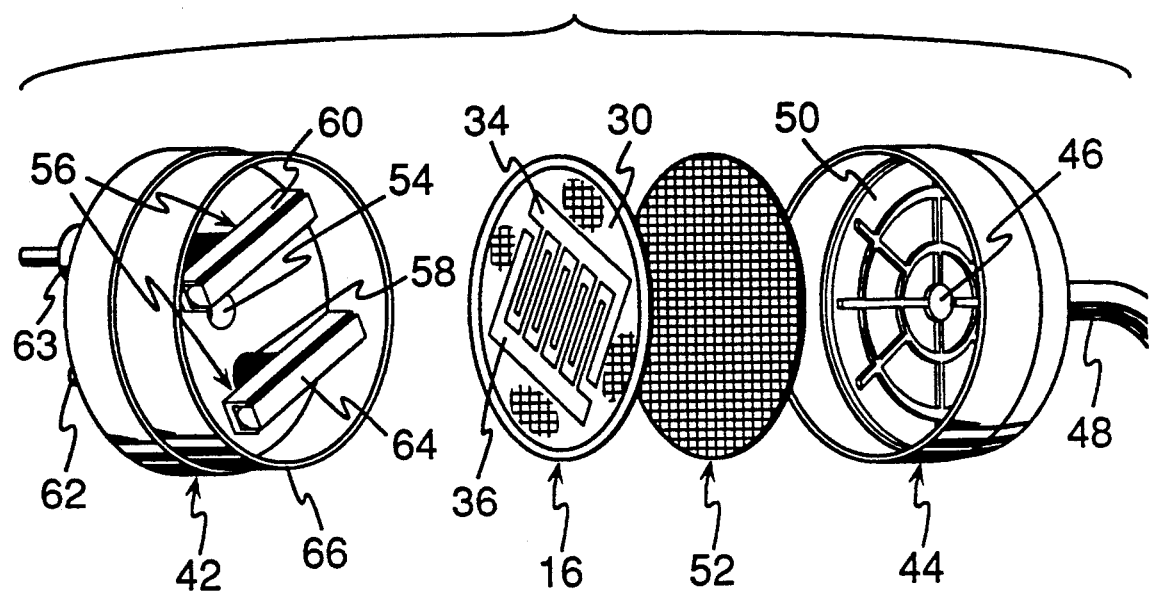
FIG. 3 is a perspective view of a disassembled conductive-particulate monitoring cell of the invention.

The filter element 16 can be used in an air-monitoring cassette, illustrated in perspective in FIG. 3, which has been modified from one available from Gelman Sciences, Inc. as Model 4336. The cassette includes a cylindrical plastic inlet cup 42 which snugly fits within a cylindrical plastic outlet cup 44. An outlet 46 at the bottom of the outlet cup 44 connects to a tapered nipple on the back side of the outlet cup 44 to which is fit a flexible tube 48 connected to the aspirator 10 during operation of the filter cassette. The bottom of the outlet cup 44 also includes a number of raised mesas 50 separated by air passages.

The inlet cup 42 includes an inlet 54 through which air can be drawn from the exterior. The standard inlet cup has been modified by the addition of two electrode assemblies 56. Each electrode assembly 56 includes a threaded pipe 58 threaded into a respective tapped hole at the bottom of the inlet cup 42. A channeled electrode 60 is brazed at the center of its rear to an electrode rod 62 which rotatably fits within the threaded pipe 58 and extends out the rear of the threaded pipe 58 for connection to electrical leads to the ohmmeter 22. A collar 63 with set screw is attached to the electrode rod 62 near the exterior end of the threaded pipe 58 to prevent the electrode assembly 56 from falling out of the threaded pipe 58. A conductive rubber cushion 64 fits within the channel of the channeled electrode 60 and extends slightly above its two legs. The rubber cushion 64 is made of a silver-filled silicone elastomer available from Tecknit, a TWP company, of Cranford, N.J. under the trade name CONSIL-R as part number 85-10507. The entire electrode assembly 56 with the exception of the rubber cushion bumper 64 is made of brass.

When the cassette is assembled, a porous cellulose support pad 52 is placed on the mesas 50 within the outlet cup 44. The filter element 16 is placed on the support pad 52 with its upstream side bearing the electrode pattern facing the electrode assemblies 56 of the inlet cup 42. The two electrode assemblies 56 and the inlet cup 42 are all rotated so that the two channeled electrodes 60 are respectively aligned with the two pads 34 and 36 of the electrode pattern. When the inlet cup 42 is placed within the outlet cup 44, its lip 66 presses the plastic collar 32 of the filter element 16 against the support pad 52 butted against the outlet cup 44 but leaves exposed the central porous membrane 30 and the electrode pattern on it so that all the air flows through the filter element 16. Knurled knobs are attached to the exteriors of the threaded pipes 58. When they are turned, the pipes 58 are adjustably threaded through the back of the inlet cup 42 to provide adjustment of the pressure of the conductive rubber cushions 64 against the electrode pads 34 and 36 supported on the backside of the filter element 16 by the support pad 52.

In operation, an aspirator is connected to the flexible tubing 48 so as to draw ambient air through the inlet 54 and through at least the portions of the porous membrane 30 between the fingers 38 and 40 of the electrode pattern. The ohmmeter 22, seen in FIG. 1, measures the resistance or conductivity (that is, current vs. voltage characteristics) of the particles deposited on the filter element 16. A capacitance meter could measure dielectric characteristics of the dust. An impedance meter could measure a complex electrical characteristic of the dust at DC or at one or more frequencies.

Although the described embodiment was designed for sampling an environment for a set sampling time and then measuring the resistance, the invention may be applied to a cumulative measurement in which the pump is continuously operated over long periods of time. The resistance is then monitored either continuously or at set periods.

This procedure could also be used as a failure analysis tool, whereby contaminant particles are transferred from a failed circuit board to a filter media and the conductivity of the particles on the filter is measured when the filter is still in the housing or alternatively removed from the housing. The dust can be more fully characterized using various tests including resistance measurements as a function of humidity to determine the hygroscopicity of the dust.

The described embodiment could be improved by using filters and filter cassettes of rectangular shape which would allow automatic alignment of the electrode assemblies with the electrode pads of the filter. The pump control and resistance measurement could be computerized to allow automatic data collection. The filter pore size could be adjusted for the environment being tested. Pore sizes of between 0.45 μm and 5 μm are common for air monitoring cassettes.

The invention thus provides a simple, quick, and inexpensive way to monitor conductive airborne contaminants.

What is claimed is:

1. An apparatus for electrically measuring conductive particles carried in a fluid, comprising
   a planar filter for filtering said particles from said fluid as said fluid passes from an upstream side to a downstream side of said filter;
   a pair of electrodes formed on and fixed to said upstream side of said filter and separated from each other by a sampling portion of said filter; and
   means electrically connected to said electrodes for measuring the conductivity of said particles deposited on said sampling portion of said filter.

2. An apparatus for electrically characterizing particles carried in a gas and comprising:
   a planar filter for filtering said particles from said gas as said gas passes from an upstream side to a downstream side of said filter;
   a pair of electrodes formed on and fixed to said upstream side of said filter and separated from each other by a sampling portion of said filter;
   a chamber detachably holding said filter within an interior of said chamber; and
   two electrical leads detachably contacting said electrodes and electrically connecting said electrodes to an exterior of said chamber while said filter is being held within said interior of said chamber.

3. An apparatus as recited in claim 2, further comprising a pump for pumping said gas from said upstream side to said downstream side of said filter held within said interior of said chamber.

4. An apparatus as recited in claim 3, further comprising electrical measuring means connected across said electrical leads.

5. An apparatus as recited in claim 2, wherein said electrodes comprise first and second sets of electrode fingers interdigitated between said sets.

6. An apparatus as recited in claim 5, wherein said filter comprises pores having sizes within a range of 0.45 to 5 μm.

7. For use in an apparatus for measuring conductive airborne contaminants in which air is drawn along an air-flow path through a chamber, a filter element comprising:
   a filtering medium disposable to block said air-flow path; and
   a set of interdigitated electrodes permanently formed on a surface of said filtering medium and electrically contactable with respective contact elements connected to said chamber.

8. A method of measuring conductive airborne contaminants, comprising the steps of:
   drawing air from an upstream side to a downstream side of a filter element comprising a porous medium and a set of electrodes formed on said upstream side of said filter element; and
   measuring an electrical characteristic between said electrodes.

9. A method as recited in claim 8, wherein said drawing step draws said air through a conduit in which said filter element is disposed and said measuring step measures said characteristic while said filter element is disposed in said conduit.

10. A method as recited in claim 9, wherein said measuring step is performed while said drawing step continues.

* * * * *